(12) United States Patent
Chu et al.

(10) Patent No.: US 10,219,786 B2
(45) Date of Patent: Mar. 5, 2019

(54) METHODS FOR OPTIMIZING GAIN OF ULTRASOUND IMAGES AND AUTOMATIC GAIN OPTIMIZATION APPARATUSES FOR ULTRASOUND IMAGING

(71) Applicant: SHENZHEN MINDRAY BIO-MEDICAL ELECTRONICS CO., LTD., Shenzhen (CN)

(72) Inventors: Xia Chu, Shenzhen (CN); Maodong Sang, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 699 days.

(21) Appl. No.: 14/732,516

(22) Filed: Jun. 5, 2015

(65) Prior Publication Data

US 2015/0265252 A1 Sep. 24, 2015

Related U.S. Application Data

(63) Continuation of application No. PCT/CN2013/083877, filed on Sep. 22, 2013.

(30) Foreign Application Priority Data

Dec. 5, 2012 (CN) .......................... 2012 1 0514756

(51) Int. Cl.
*A61B 8/08* (2006.01)
*A61B 8/00* (2006.01)
(Continued)

(52) U.S. Cl.
CPC .............. *A61B 8/5269* (2013.01); *A61B 8/14* (2013.01); *A61B 8/461* (2013.01); *A61B 8/5207* (2013.01);
(Continued)

(58) Field of Classification Search
None
See application file for complete search history.

(56) References Cited

U.S. PATENT DOCUMENTS 6,322,509 B1 * 11/2001 Pan ...................... A61B 5/1075
600/443
6,679,844 B2 1/2004 Loftman et al.
(Continued)

FOREIGN PATENT DOCUMENTS

| CN | 101972152 A | 2/2011 |
| CN | 101987023 A | 3/2011 |
| CN | 102499711 A | 6/2012 |

*Primary Examiner* — Katherine Fernandez
(74) *Attorney, Agent, or Firm* — Polsinelli LLP; Kory D. Christensen

(57) ABSTRACT

Methods for optimizing gain of an ultrasound image may include: acquiring a tissue image and a first noise image under a same imaging condition; de-noising the tissue image by the first noise image to obtain a de-noised tissue image; identifying a tissue region in the de-noised tissue image; determining whether a percentage of the tissue region in the de-noised tissue image exceeds a preset threshold condition; selecting, according to the determination result, a corresponding calculation method to calculate a first master gain and a first time gain compensation (TGC) curve for the tissue image; and applying the first TGC curve and the first master gain obtained through calculation to the tissue image acquired before.

21 Claims, 7 Drawing Sheets

(51) Int. Cl.
    *G01S 7/52*    (2006.01)
    *A61B 8/14*    (2006.01)
    *G06T 5/00*    (2006.01)

(52) U.S. Cl.
    CPC ............ *A61B 8/54* (2013.01); *G01S 7/52033* (2013.01); *G06T 5/002* (2013.01); *A61B 8/481* (2013.01); *G06T 2207/10132* (2013.01); *G06T 2207/30004* (2013.01)

(56) References Cited

U.S. PATENT DOCUMENTS

| | | | |
|---|---|---|---|
| 2003/0236459 A1* | 12/2003 | Loftman | G01S 7/52026 600/437 |
| 2009/0076387 A1 | 3/2009 | Simopoulos | |
| 2011/0054317 A1* | 3/2011 | Lin | G01S 7/52033 600/443 |
| 2014/0066767 A1* | 3/2014 | Mammone | G01S 7/52033 600/442 |

\* cited by examiner

METHODS FOR OPTIMIZING GAIN OF ULTRASOUND IMAGES AND AUTOMATIC GAIN OPTIMIZATION APPARATUSES FOR ULTRASOUND IMAGING

TECHNICAL FIELD

This disclosure relates to ultrasound image optimization, and particularly to methods for optimizing gain of ultrasound images and automatic gain optimization apparatuses for ultrasound imaging.

BACKGROUND

Gain adjustment is important for ultrasound imaging. Correspondingly, ultrasound imaging systems may be generally provided with a fixed gain that is suitable for a majority of subjects. Since ultrasonic waves may be attenuated to a different extent within each patient, however, the fixed gain predetermined in the systems may not be suitable in all cases. At this point, users may need to manually adjust time gain compensation (TGC), lateral gain compensation (LGC) and a master gain. Such manual adjustment is time-consuming, and an optimal gain curve may not be obtained in this case, where automatic gain optimization can overcome these drawbacks and automatic gain optimization function may thus be equipped for many ultrasound imaging systems. However, automatic gain optimization is mostly applied to B-mode ultrasound images, and most of the methods for automatically optimizing the gain may obtain a gain compensation curve by counting image brightness and noise information and then calculating differences between target brightness and brightness of a tissue region.

Contrast imaging, overcomes various drawbacks of conventional imaging, such as not being able to display blood flow and/or not being able to display micro-vessels. The contrast imaging may obtain and display blood flow information and vessel distribution within a human body using a non-linear detection technology to detect some micro-bubbles that may have a size similar to blood cells and be injected into the human body. The contrast imaging may be generally operated under a low mechanical index, so that the micro-bubbles can be prevented from being destroyed by sound waves. Due to the low mechanical index, emitted energy for the contrast imaging may also be low, and thus a signal to noise ratio (SNR) of the contrast imaging may be lower than that of the conventional B-mode ultrasound image. Besides, it is difficult to apply the method for optimizing the gain of the conventional B-mode ultrasound image to the contrast image. Moreover, as a concentration of the micro-bubbles changes within the human body before or after injecting a contrast agent, brightness of a contrast image may vary correspondingly. In this case, the conventional methods for automatically optimizing the gain by counting image brightness cannot be applied to the contrast image.

Some conventional methods for automatically optimizing the gain of the contrast image may be based on the relation between the brightness of the contrast image and the contrast agent. When the image brightness is greater than a preset value or an amount of the contrast agent reaches a preset value, the contrast image may be processed by the method for automatically optimizing the gain of the conventional B-mode images; alternatively, the brightness may be adjusted according to noise information. However, this may lead to different brightness compensation for a same patient since different optimization methods are started at each stage.

The contrast imaging can often generate two kinds of images: a tissue image representing tissue information and a contrast image representing contrast agent information, where a same gain curve may be applied to those two images up to now. Due to different characteristics of the contrast image and the tissue image, however, the gain curve set according to the tissue image may not be suitable for the contrast image. For example, brightness of the contrast image may vary before the micro-bubbles are injected and as the micro-bubbles get enhanced or decreased; and/or the contrast image and the tissue image may have different attenuation characteristics. Therefore, different gain curves may be required according to different image characteristics.

SUMMARY OF THIS DISCLOSURE

This disclosure provides methods for optimizing gain of ultrasound images and automatic gain optimization apparatuses for ultrasound imaging, which can improve the gain optimization of the ultrasound images, so that the gain optimization of a tissue image can adapt for different situations and brightness of contrast images of different subjects can be consistent with each other after the gain optimization.

In one aspect, a method for optimizing gain of an ultrasound image may include:

acquiring a tissue image and a first noise image in a same imaging condition;

de-noising the tissue image by the first noise image to obtain a de-noised tissue image;

identifying a tissue region in the de-noised tissue image;

determining whether a percentage of the tissue region in the de-noised tissue image exceeds a preset threshold condition;

selecting, according to the determination result, corresponding calculation methods to calculate a first master gain and a first TGC curve for the tissue image; and applying the first TGC curve and the first master gain obtained through calculation to the tissue image acquired before.

In some embodiments, the tissue image can be a tissue image representing tissue information obtained during ultrasound contrast imaging, or the tissue image can be a fundamental image or a harmonic image obtained during B-mode imaging.

In some embodiments, in order to de-noise the tissue image by the first noise image, an average value of each line of the first noise image may be calculated to obtain a first noise average value curve, and the first noise average value curve may be subtracted from the tissue image to obtain the de-noised tissue image.

In some embodiments, the de-noised tissue image can be partitioned into multiple image sub-blocks along a horizontal direction and a longitudinal direction, statistical parameters may be calculated for each image sub-block, and adaptive thresholds to be used for region identification may be determined according to the statistical parameters of each image sub-block. After that, the statistical parameters of each image sub-block may be compared with the adaptive thresholds to determine a region, to which each image sub-block belongs, to be a noise region, a boundary region, a low-echo region or the tissue region.

In some embodiments, the statistical parameters may include an average value, a standard deviation and a signal to noise ratio of each image sub-block, and the adaptive thresholds may include a noise threshold, a high threshold for standard deviation, a high threshold for average value and a low threshold for average value.

In some embodiments, the region to which each image sub-block belongs to may be determined as follows: one of the image sub-blocks where the signal to noise ratio is smaller than the noise threshold may be determined to be a noise block and thus to belong to the noise region; one of the image sub-blocks where the standard deviation is larger than the high threshold for standard deviation or the average value is larger than the high threshold for average value may be determined to be a boundary block and thus to belong to the boundary region; one of the image sub-blocks where the average value is smaller than the low threshold for average value may be determined to be a low-echo block and thus to belong to the low-echo region; or one of the image sub-blocks that fails to meet the three previous determination conditions may be determined to be a tissue block and thus to belong to the tissue region.

In some embodiments, the noise threshold may be manually set according to a signal to noise ratio of the noise region.

In some embodiments, the high threshold for standard deviation is calculated as follows: THstdH=mean(Std_Xm)+P*std(Std_Xm); the high threshold for average value is calculated as follows: THmeanH=mean(Mean_Xm)+P*std(Mean_Xm); and the low threshold for average value is calculated as follows: THmeanL=mean(Mean_Xm)−P*std(Mean_Xm);

where Std_Xm represents a standard deviation of an $m^{th}$ image sub-block, mean(Std_Xm) represents an average value of the standard deviations of all the image sub-blocks, std(Std_Xm) represents a total standard deviation of the standard deviations of all the image sub-blocks, Mean_Xm represents an average value of the $m^{th}$ image sub-block, mean(Mean_Xm) represents an average value of the average values of all the image sub-blocks, std(Mean_Xm) represents a standard deviation of the average values of all the image sub-blocks, m is in a range of 1 to M, M represents a total block quantity of the image sub-blocks partitioned from the de-noised tissue image, and P represents an adjustable parameter that is set according to a signal distribution range within the tissue image.

In some embodiments, the method may further include removing data of the noise block when calculating the high threshold for standard deviation, the high threshold for average value and the low threshold for average value.

In some embodiments, the adjustable parameter P can be inversely proportional to the signal distribution range within the tissue image.

In some embodiments, it may be determined whether the percentage of the tissue region in the de-noised tissue image exceeds the preset threshold condition as follows: counting a block quantity of the tissue block(s) in each line of the image sub-blocks; determining a line to be a tissue valid line when a ratio between the block quantity of the tissue block(s) and a block quantity of the image sub-blocks along the line is larger than a first threshold; and determining the percentage of the tissue region in the de-noised tissue image to exceed the preset threshold condition when a ratio between a line number of all the tissue valid line(s) and a line number of all the image sub-blocks is larger than a second threshold.

In some embodiments, when the percentage of the tissue region in the de-noised tissue image exceeds the preset threshold condition, the first master gain may be a difference value between tissue target brightness and an average value of all the tissue regions.

In some embodiments, when the percentage of the tissue region in the de-noised tissue image fails to exceed the preset threshold condition, the first master gain is a difference value between a noise target brightness and a minimum value of a longitudinal tissue average value curve, where the longitudinal tissue average value curve represents average values of each line of the tissue image.

In some embodiments, when the percentage of the tissue region in the de-noised tissue image exceeds the preset threshold condition, the first TGC curve is calculated according to distributions of the tissue region and the noise region.

In some embodiments, when the percentage of the tissue region in the de-noised tissue image fails to exceed the preset threshold condition, the first TGC curve is calculated using a noise equalization method.

In some embodiments, when the percentage of the tissue region in the de-noised tissue image exceeds the preset threshold condition, the first TGC curve can be calculated as follows: calculating a longitudinal average value curve, calculating a target brightness curve, and calculating the first TGC curve by subtracting a first noise average value curve and the longitudinal average value curve from the target brightness curve, where the first noise average value curve represents average values of each line of the first noise image.

In some embodiments, an average value of the tissue blocks in a tissue valid line may be taken as a value of the longitudinal average value curve corresponding to the tissue valid line. In some embodiments, an average value of the noise blocks in a noise valid line may be taken as a value of the longitudinal average value curve corresponding to the noise valid line, where the noise valid line is defined as a ratio between a block quantity of the noise block(s) and the block quantity of the image sub-blocks in the noise valid line is larger than the first threshold. In some embodiments, an average value of the tissue blocks in a line may be taken as a value of the longitudinal average value curve corresponding to the line when the line is both a tissue valid line and a noise valid line. In some embodiments, a linear interpolation of other line(s) may be taken as a value of the longitudinal average value curve corresponding to other line(s) when other line(s) is(are) neither a tissue valid line nor a noise valid line, where the linear interpolation of other line(s) is(are) obtained using an average value of the tissue valid line(s) and/or the noise valid line(s) that is(are) adjacent to said other line(s).

In some embodiments, target brightness of each line may be determined according to image property of each line so as to calculate the target brightness curve. Target brightness of the tissue valid line can be substantially equal to tissue target brightness, target brightness of the noise valid line can be substantially equal to noise target brightness, and target brightness of other line(s) can be obtained through interpolation using the target brightness of the tissue valid line(s) and/or noise valid line(s).

In some embodiments, a first noise average value curve and the longitudinal average value curve may be subtracted from the target brightness curve to obtain the first TGC curve, where the first noise average value curve can represent average values of each line of the first noise image.

In some embodiments, when the percentage of the tissue region in the de-noised tissue image fails to exceed the preset threshold condition, the first TGC curve may be calculated as follows: an attenuation value of the tissue image may be calculated through multiplying a tissue attenuation coefficient by a transmission frequency and image depth; a tissue noise target brightness curve which may be an equal interpolation oblique line between zero and the attenuation value of the tissue image can then be calculated; and a first noise average value curve may be subtracted from the tissue noise target brightness curve to obtain the first TGC curve, where the first noise average value curve represents average values of each line of the first noise image.

In another aspect, a method for optimizing gain during ultrasound contrast imaging may include performing gain optimization for a tissue image using the above-described method and performing gain optimization for a contrast image. The gain optimization of the contrast image may include:

acquiring the contrast image and a second noise image under a same imaging condition during the ultrasound contrast imaging;

calculating a second master gain and a second TGC curve for the contrast image, where the second master gain of the contrast image is substantially equal to a difference value (i.e., D-value) between contrast target brightness and the first master gain of the tissue image; and applying the second TGC curve and the second master gain obtained through calculation to the contrast image acquired before.

In some embodiments, an attenuation value of the contrast image may be calculated through multiplying a contrast attenuation coefficient by a transmission frequency and image depth. A contrast noise target brightness curve which may be an equal interpolation oblique line between zero and the attenuation value of the contrast image can then be calculated. A second noise average value curve may be subtracted from the contrast noise target brightness curve to obtain the second TGC curve, where the second noise average value curve represents average values of each line of the second noise image.

In still another aspect, an automatic gain optimization apparatus for ultrasound imaging may include a first image processing module, a second image processing module, a first image output module and a second image output module.

The first image processing module can receive image information, calculate the first master gain and the first TGC curve of the tissue image according to the above-described method for optimizing the gain of the ultrasound image, transmit the first TGC curve and the first master gain obtained through calculation to the first image output module, and transmit the first master gain of the tissue image to the second image processing module.

The first image output module can apply the first master gain and the first TGC curve of the tissue image to the acquired tissue image, and output the tissue image with optimized gain through an output port.

The second image processing module can receive the image information, calculate the second master gain and the second TGC curve of the contrast image according to the above-described method for optimizing the gain during the ultrasound contrast imaging, and transmit the second TGC curve and the second master gain obtained through calculation to the second image output module.

The second image output module can apply the second master and gain the second TGC curve of the contrast image to the acquired contrast image, and output the contrast image with optimized gain through the output port.

The first image processing module and the second image processing module can connect with an input port, the first image output module and the second image output module can connect with the output port, the first image processing module can connect with the first image output module, the second image processing module can connect with the second image output module, and the first image processing module can also connect with the second image processing module.

In some embodiments, the image information may be a fundamental image or a harmonic image and a corresponding first noise image obtained during B-mode imaging. In some embodiments, the image information may be the tissue image and a corresponding first noise image obtained during the ultrasound contrast imaging.

In yet another aspect, an ultrasound imaging system can include the above-described automatic gain optimization apparatus for ultrasound imaging. The ultrasound imaging system can also include a transmission control module, an ultrasound probe, a signal receiving module, a signal processing module, a postprocessing module and a display module, where the transmission control module, the ultrasound probe, the signal receiving module, the signal processing module, the automatic gain optimization apparatus for ultrasound imaging, the postprocessing module and the display module can be connected successively.

The method for optimizing the gain of the ultrasound image can adaptively determine thresholds for different regions according to the image information and automatically divide the image into four regions (a boundary region, a tissue region, a low echo region and a noise region). The region division (also called as region identification) can be more accurate since the differences between the thresholds of different images are taken into consideration, and the region identification can be suitable for multiple kinds of ultrasound images obtained during the B-mode imaging and the contrast imaging. Besides, the gain optimization method determined based on the percentage of the tissue region in the de-noised tissue image can ensure complete display of the image information and meet the equalization demand on the brightness of the optimized image.

Embodiments of this disclosure can correct an adjustment parameter of the contrast image using a gain adjustment parameter of the tissue image. In this case, the brightness of the contrast images of different subjects can be made substantially uniform after the gain optimization, thereby greatly improving scan efficiency.

BRIEF DESCRIPTION OF THE DRAWINGS

Following detailed descriptions of respective embodiments in this disclosure can be understood better when combined with these figures, in which the same structure is represented by the same reference sign. In the figures.

DETAILED DESCRIPTION

This disclosure is described clearly and thoroughly with reference to accompanying drawings in various embodiments herein. It is apparent that those embodiments are merely a part of this disclosure. Those skilled persons in the art can obtain any other embodiments without spending inventive efforts based on those embodiments listed below, and all these other embodiments should fall within the scope of this disclosure.

Gain adjustment is important for ultrasound imaging, and gain control during the ultrasound imaging may often include master gain for controlling overall image brightness, lateral gain compensation (LGC) for equalizing image brightness along a horizontal direction, and/or time gain compensation (TGC, which is also called depth gain compensation (DGC)) for compensating signal attenuation along a depth direction during signal propagation. The TGC can further include analog time gain compensation (ATGC) and digital time gain compensation (DTGC). The gain adjustment described in various embodiments of this disclosure mainly relates to digital gain, which may mainly include the master gain and the DTGC of the TGC.

Figure 1:
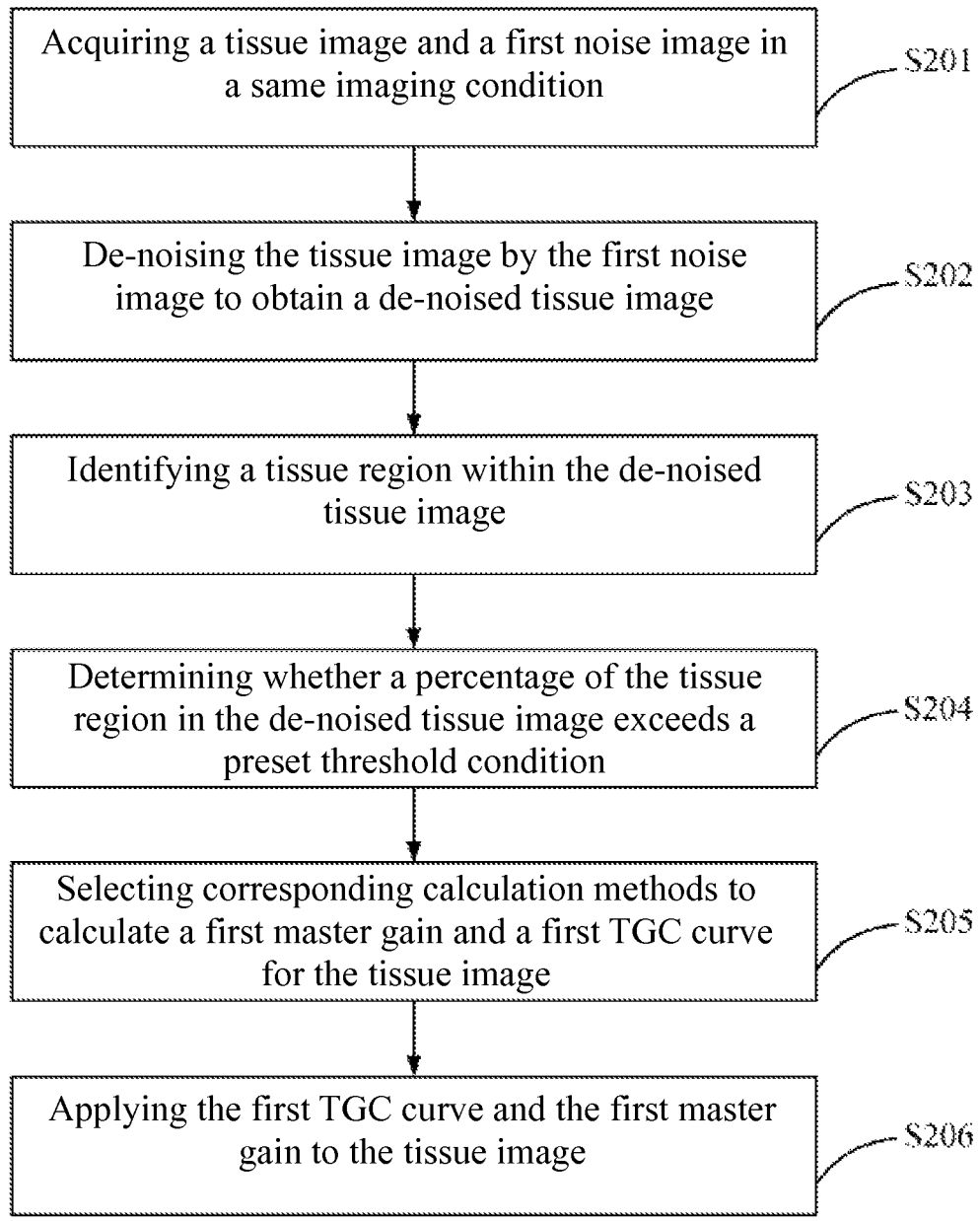
FIG. 1 is a flow chart illustrating a method for optimizing gain of an ultrasound image according to a first embodiment of this disclosure.

As shown in FIG. 1, a method for optimizing gain of an ultrasound image can be provided according to a first embodiment of this disclosure. The method may include steps S201 to S206.

In step S201, a tissue image and a first noise image can be acquired under a same imaging condition.

In step S202, the tissue image can be de-noised using the first noise image to obtain a de-noised tissue image.

In step S203, a tissue region can be identified within the de-noised tissue image.

In step S204, it can be determined whether a percentage of the tissue region in the de-noised tissue image exceeds a preset threshold condition.

In step S205, a corresponding calculation method can be selected according to a determination result in step S204 to calculate a master gain and a TGC curve for the tissue image.

In step S206, the TGC curve and the master gain obtained through the calculation in step S205 can be applied to the tissue image acquired in step S201.

The tissue image acquired in step S201 may be a tissue image representing tissue information obtained during ultrasound contrast imaging, or the tissue image acquired in step S201 can be a fundamental image or a harmonic image obtained during B-mode imaging. The first noise image may be acquired when stopping transmitting ultrasonic waves under the same imaging condition as the tissue image. The tissue images obtained during the contrast imaging and the B-mode imaging may have different mechanical indexes, where a low mechanical index may be used for the contrast imaging so as to prevent contrast micro-bubbles from being destroyed by a sound pressure. Here, different emitted energies can be obtained under different mechanical indexes, which may further lead to different signal to noise ratios of the images. The method for optimizing the gain of the ultrasound image can be suitable for the tissue images obtained during both the contrast imaging and the B-mode imaging in embodiments of this disclosure.

In step S202, for the purpose of de-noising processing, an average value of each line of the first noise image can be calculated to obtain a first longitudinal noise average value curve, which can then be processed into a smoothed noise average value curve through low-pass filtering; after that, the first noise average value curve can be subtracted from the tissue image to obtain the de-noised tissue image.

The noise herein can refer to electronic noise or thermal noise. Conventional ultrasound systems may use ATGC and/or DTGC to compensate signal attenuation along a direction of propagation. In this situation, when a probe emitting ultrasonic waves is arranged to contact no subject, the noise can nearly be white noise without the action of the ATGC and the DTGC, while the noise average value curve can progressively increase with the depth under the influence of the ATGC and the DTGC. The ATGC and the DTGC can enhance both far field noise and image signal. Therefore, in order to obtain real signals, subtracting the noise average value curve from the tissue image may not only aim at removing noise, but also eliminating the signal influence from the ATGC and the DTGC.

Classification of the regions within the tissue image may be considered when identifying the tissue region in step S203. In embodiments of this disclosure, the tissue image can be divided into a noise region, a boundary region, a low-echo region and a tissue region, where the low-echo region is an extra one compared to the prior art. The low-echo region can be substantially deemed as belonging to the tissue region, which however has an average value larger than that of the noise region and lower than that of the tissue region. The low-echo regions may always have lower brightness caused by sound wave attenuation, poor probe contact or sound wave shading along a forward direction. In the conventional method for optimizing the gain of the ultrasound image, however, the image regions may be divided into the noise region, the boundary region and the tissue region, and image sub-block(s) belonging to the low-echo region may be defined as another region. This may cause great calculation error and thus affect the gain optimization effect.

Figure 2:
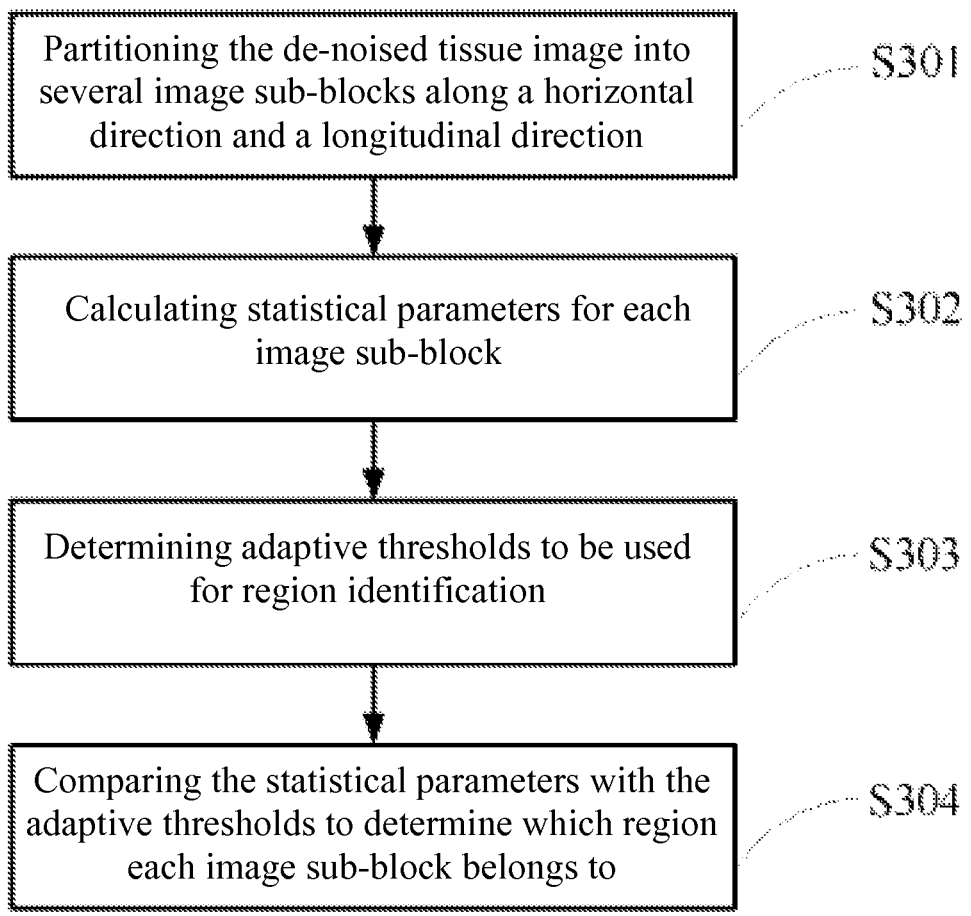
FIG. 2 is a flow chart illustrating the step S203 in FIG. 1.

As shown in FIG. 2, step S203 can further include steps S301 to S304.

In step S301, the de-noised tissue image can be partitioned into several image sub-blocks along a horizontal direction and a longitudinal direction.

In step S302, statistical parameters can be calculated for each image sub-block.

In step S303, adaptive thresholds used for region identification can be determined according to the statistical parameters of each image sub-block in step S303.

In step S304, the statistical parameter(s) of each image sub-block calculated in step S302 can be compared with the adaptive threshold(s) obtained in step S303, so as to determine whether each image sub-block may belong to the noise region, the boundary region, the low-echo region or the tissue region.

The image partition in step S301 may function as improving a calculation speed and statistical robustness. Dimension of the image sub-block can affect following calculation. In the case where there are too many sub-blocks, the statistical data may become unstable; in the case of too few sub-blocks, there may be too many invalid sub-blocks and useful information cannot be formed. Suitable block quantity can be used for image partition according to the specific tissue image to be optimized.

The de-noised tissue image can be distinguished into various regions according to brightness, square deviation and SNR. In this way, the statistical parameters in step S302 can include an average value, a standard deviation and an SNR of each image sub-block. Here, such parameters can be calculated as follows.

The average value (which refers to an average value of all the pixel points within each image sub-block):

$$\text{Mean\_}Xm=(x1+x2+\ldots+xn)/n.$$

The standard deviation:

$$\text{Std\_}Xm=\{[(x1-\text{Mean\_}Xm)^2+(x2-\text{Mean\_}Xm)^2+\ldots+(xn-\text{Mean\_}Xm)^2]/n\}^{1/2}.$$

The SNR:

$$\text{SNR}=20*\log 10(\text{signal}/\text{noise})=20*\log 10(\text{signal})-20*\log 10(\text{noise}).$$

In such formulas, xi (i=1–n) represents a value of each pixel point within the image sub-block, n represents the quantity of the pixel points within each image sub-block, Mean_Xm (m=1–M) represents the average value of an $m^{th}$ image sub-block, Std_Xm (m=1–M) represents the standard deviation of the $m^{th}$ image sub-block, M represents a total block quantity of the image sub-blocks partitioned from the de-noised tissue image in step S301, signal refers to a tissue image curve, and noise refers to a corresponding noise image curve.

After the calculation of such statistical parameters, which region the respective image sub-block may belong to can be determined. The determination method can affect the accuracy of the region identification; for example, threshold selection can have significant influence on the accuracy of the region identification. Conventionally, a fixed threshold may be utilized to be compared with the statistical parameters of each image sub-block, so that the region to which each image sub-block may belong can be determined. However, the fixed threshold cannot adapt for all the images, and thus inaccurate region identification may be caused using the fixed threshold in some situations, which may further affect the tissue image optimization. The adaptive threshold can be used for determining the region which the image sub-block may belong to in embodiments of this disclosure, in which case a threshold range can be respectively determined for different regions according to image content or pixel distribution.

In step S303, the adaptive thresholds can include a noise threshold, a high threshold for standard deviation, a high threshold for average value and a low threshold for average value, where all of the high threshold for standard deviation, the high threshold for average value and the low threshold for average value can be adaptively determined according to the image content. Herein, each adaptive threshold can be determined as follows.

The noise threshold can be manually set according to an SNR of the noise region.

The high threshold for standard deviation:

$$TH\text{std}H=\text{mean}(\text{Std\_}Xm)+P*\text{std}(\text{Std\_}Xm).$$

The high threshold for average value:

$$TH\text{mean}H=\text{mean}(\text{Mean\_}Xm)+P*\text{std}(\text{Mean\_}Xm).$$

The low threshold for average value:

$$TH\text{mean}L=\text{mean}(\text{Mean\_}Xm)-P*\text{std}(\text{Mean\_}Xm).$$

In such expressions, Std_Xm (m=1–M) represents the standard deviation of the $m^{th}$ image sub-block, mean(Std_Xm) represents an average value of the standard deviations of all the image sub-blocks, std(Std_Xm) represents a total standard deviation of the standard deviations of all the image sub-blocks, Mean_Xm (m=1–M) represents the average value of the $m^{th}$ image sub-block, mean(Mean_Xm) represents an average value of the average values of all the image sub-blocks, std(Mean_Xm) represents a standard deviation of the average values of all the image sub-blocks, M represents the total block quantity of the image sub-blocks partitioned from the de-noised tissue image in step S301, and P represents an adjustable parameter that can be set according to a signal distribution range within the tissue image.

It can be known that a far field portion of the image may belong to the noise region having noise or no content. Provided that a percentage of the noise region is too large in the image, apparent influence may be caused to the threshold determination for the average value and the standard deviation. In this case, the noise region may be removed before calculating the adaptive thresholds; that is, the data of noise blocks may be left out when calculating the high threshold for standard deviation, the high threshold for average value and the low threshold for average value. Here, the image sub-block which has an SNP lower than the noise threshold can be deemed as the noise block.

During the above-described determination of the adaptive thresholds, it is presumed that the value of each pixel point within the image is a random variable, and thus the average value and the standard deviation of each image sub-block are also random variables. The random variable may approximately have a normal distribution in which substantially 68% of the values are within a range of one standard deviation from the average value and substantially 95% of the values are within a range of two standard deviations from the average value. Therefore, a signal range can be determined according to the average value and the standard deviation. Accordingly, a threshold range for the average value can be a combination of an average value and standard deviation of the average values of all the sub-blocks, where P can be an adjustable parameter for selecting a range of P standard deviation(s) from the average value. The threshold range for the standard deviation can be determined in the same way. The value of P can be selected with respect to the content or an examination mode of the tissue image, and thus manual setting can be required for determining the P value. For example, the P value can be large in a liver mode since the signal distribution range is relatively small except a boundary of a liver capsule; the P value can become small in a kidney mode due to a relatively large signal distribution range. That is, the value of the adjustable parameter P can be inversely proportional to the signal distribution range of the (de-noised) tissue image.

After the adaptive threshold is determined, the region to which each image sub-block belongs can be determined in step S304 as follows.

The image sub-block of which the SNP is smaller than the noise threshold may be deemed as the noise block, and thus the corresponding image sub-block may belong to the noise region.

The image sub-block of which the standard deviation is larger than the high threshold for standard deviation or the average value is larger than the high threshold for average value may be deemed as a boundary block, and thus the corresponding image sub-block may belong to the boundary region.

The image sub-block of which the average value is smaller than the low threshold for average value may be deemed as a low-echo block, and thus the corresponding image sub-block may belong to the low-echo region.

The image sub-block failing to meet such three conditions may be deemed as a tissue block, and thus the corresponding image sub-block may belong to the tissue region.

In the above-described determination method, it is first determined that the image sub-block having low average value may be the noise region; the image sub-block having large standard deviation or large average value can then be determined as the boundary region since the boundary region can be significantly characterized in large standard deviation (the boundary region can have the largest acoustic impedance difference and thus it may exhibit as highlighting echo during ultrasound imaging); the image sub-block of which the average value is larger than the noise threshold and smaller than the low threshold for average value can then be determined as the low-echo region (the low-echo region may substantively belong to the tissue region, but its average value may be between those of the tissue and the noise); or the image sub-block that falls out of those three regions can be deemed as belonging to the tissue region.

In various embodiments of this disclosure, the method for determining which region the image sub-block may belong to is different from the conventional method(s). The thresholds for different regions can be adaptively determined according to the image content; in this case, different thresholds can be obtained for different image contents. The threshold can be crucial for enabling the accurate region determination and thus for enabling the whole automatic gain optimization. It can be known that the adaptive threshold can be more accurate than the fixed threshold, and thus better gain optimization can be achieved correspondingly.

In embodiments of this disclosure, two variables can be outputted through the method for optimizing the gain of the ultrasound image: the master gain for adjusting overall image brightness and the TGC curve (of which an average value can be zero) for adjusting image equalization. The TGC curve may enhance the brightness in low-echo positions and decrease the brightness in high-echo positions, so as to adjust the image equalization. Corresponding calculation of the two variables can be related to a percentage of the tissue block in the tissue image. Therefore, it may be needed to determine whether the percentage of the tissue region in the tissue image exceeds the preset threshold condition before corresponding calculation.

In step S204, in order to determine whether the percentage of the tissue region in the tissue image exceeds the preset threshold condition, a block quantity of the tissue block(s) can first be counted in each line of the image sub-blocks. When a ratio between the block quantity of the tissue block(s) and a block quantity of the image sub-blocks along a line is larger than a first threshold, the corresponding line can be deemed as a tissue valid line; when a ratio between a line number of all the tissue valid line(s) and a line number of all the image sub-blocks is larger than a second threshold, it can be determined that the percentage of the tissue region in the tissue image exceeds the preset threshold condition; or when a ratio between the line number of all the tissue valid line(s) and the line number of all the image sub-blocks is smaller than a second threshold, it can be determined that the percentage of the tissue region in the tissue image fails to exceed the preset threshold condition. Here, the first threshold can be a ratio with respect to a horizontal partition quantity (i.e., a row number of all the image sub-blocks), and the second threshold can be a ratio with respect to a longitudinal partition quantity (i.e., a line number of all the image sub-blocks). Both the first threshold and the second threshold can be manually and appropriately set according to specific imaging target on the tissue image.

The tissue information may be displayed as a gray-scale image during the ultrasound imaging. Correspondingly, the information in dB format after logarithm transformation is required to be further transformed into gray-scale information of 0-255, where this further transformation can be called as a dynamic range transformation. In the case where a dynamic range is fixed, information loss may be caused due to apparent noise and large signal saturation within the image when the master gain of the signal is too large; instead, low-echo signals may be lost when the master gain is too small. Therefore, the adjustment of the master gain may be important for the ultrasound image optimization.

The master gain may be adjusted to display all the information within the image to the largest extent, so that a minimum value (i.e., noise target brightness) can be ensured for the noise during the dynamic range transformation. In the case where the image merely contains tissue information without noise, the adjustment of the master gain may aim at bringing tissue brightness into tissue target brightness. For this reason, the percentage of the tissue region in the tissue image may be determined before calculating the master gain.

In step S205, when the percentage of the tissue region in the tissue image exceeds the preset threshold condition, the master gain of the tissue image may be a difference value between the tissue target brightness and an average value of all the tissue regions. Instead, when the percentage of the tissue region in the tissue image fails to exceed the preset threshold condition, the master gain of the tissue image may be a difference value between the noise target brightness and a minimum value of a longitudinal tissue average value curve, where the longitudinal tissue average value curve can be a curve describing the average values of each line of the tissue image.

The TGC (time gain compensation) curve outputted after optimizing the gain of the ultrasound image can function as equalizing the image brightness. That is, all the tissue blocks within the tissue image can be displayed with the same brightness. When there are enough tissue blocks in the image, the tissue blocks can be displayed with equal brightness. When there are too few tissue blocks, the tissue brightness can be approximately maintained equalized using a noise equalization method. For this reason, the percentage of the tissue region in the tissue image may also be determined before calculating the TGC curve. When the percentage of the tissue region in the tissue image exceeds the preset threshold condition, the TGC curve of the tissue image can be calculated according to the distribution of the tissue region and the noise region. Otherwise, when the percentage of the tissue region in the tissue image fails to exceed the preset threshold condition, the TGC curve of the tissue image can be calculated using the noise equalization method.

Figure 3:
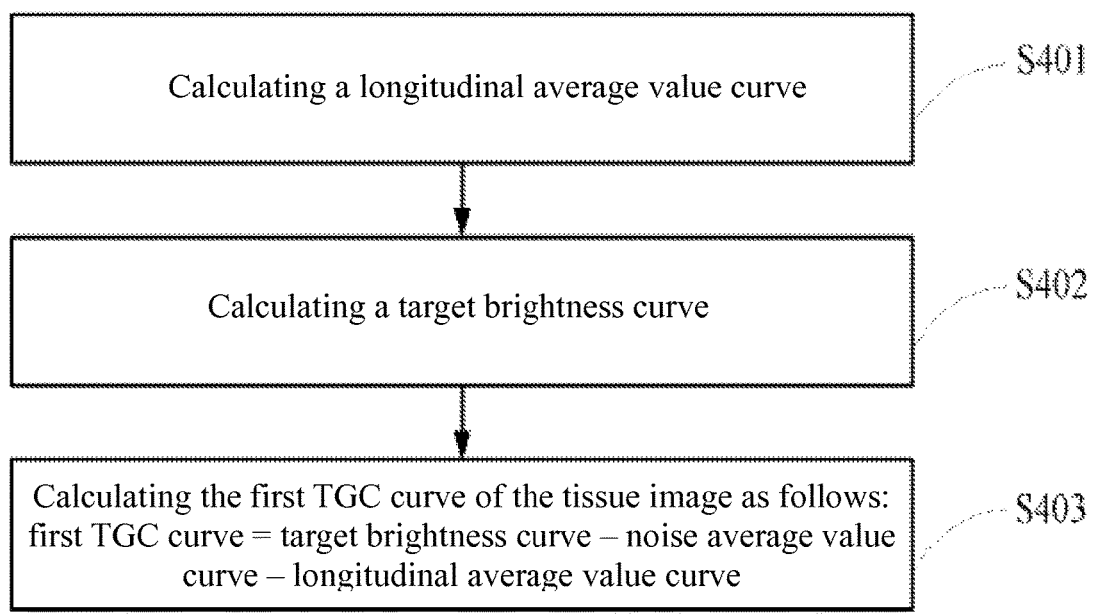
FIG. 3 is a flow chart illustrating the step S205 in FIG. 1.

As shown in FIG. 3, when the percentage of the tissue region in the tissue image exceeds the preset threshold condition, the TGC curve of the tissue image can be calculated in step S205 as follows.

In step S401, a longitudinal average value curve can be calculated.

In step S402, a target brightness curve can be calculated.

In step S403, the TGC curve can be calculated for the tissue image.

The TGC curve of the tissue image can be obtained by subtracting the first noise average value curve and the longitudinal average value curve from the target brightness curve (i.e., TGC curve of tissue image=target brightness curve−first noise average value curve−longitudinal average value curve), where the first noise average value curve can be obtained by calculating the average values of each line of the noise image and thus the first noise average value curve may represent average value variations along the longitudinal direction.

In step S401, the longitudinal average value curve can be calculated as follows:

taking the average value of the tissue blocks in the tissue valid line as a value of the longitudinal average value curve corresponding to the tissue valid line;

taking the average value of the noise blocks in a noise valid line as a value of the longitudinal average value curve corresponding to the noise valid line; when a ratio between a block quantity of the noise block(s) and the block quantity of the image sub-blocks in a certain line is larger than the first threshold, the corresponding line can be deemed as the noise valid line;

taking an average value of the tissue blocks in a line as a value of the longitudinal average value curve corresponding to this line when this line is both a tissue valid line and a noise valid line;

taking a linear interpolation of other line(s) as a value of the longitudinal average value curve corresponding to other line(s) when other line(s) is(are) neither a tissue valid line nor a noise valid line, where the linear interpolation of other line(s) can be obtained using the average value of the tissue valid line(s) and/or the noise valid line(s) that is(are) adjacent to other line(s); and performing smoothing filtering on the longitudinal average value curve and upsampling to the same line number of all the image sub-blocks along the longitudinal direction.

In step S402, the target brightness of each line can be determined according to the property of the corresponding line, where the target brightness of the tissue valid line can be substantially equal to the tissue target brightness, the target brightness of the noise valid line can be substantially equal to the noise target brightness, and the target brightness of other lines can be obtained through interpolation using the target brightness of the tissue valid line(s) and the noise valid line(s). After that, smoothing filtering can be performed for the target brightness curve, which may further be upsampled to the same line number of all the image sub-blocks along the longitudinal direction.

The target brightness curve can determine final display brightness of the image, the longitudinal average value curve can be obtained based on de-noised data, and the TGC curve may act upon the original acquired image. Therefore, the noise is required to be subtracted from the target brightness curve when calculating the TGC curve. Consequently, in step S403, the TGC curve of the tissue image can be calculated as follows: TGC curve of tissue image=target brightness curve−first noise average value curve−longitudinal average value curve, where the first noise average value curve can be obtained by calculating the average values of each line of the noise image. A normalized TGC curve can then be obtained by subtracting a curve average value from the calculated TGC curve.

Figure 4:
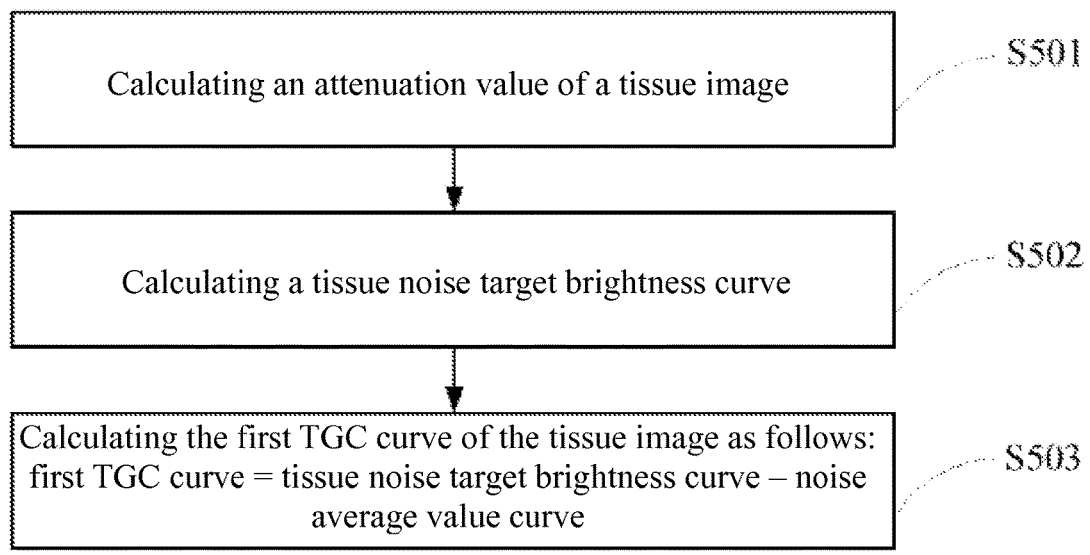
FIG. 4 is another flow chart illustrating the step S205 in FIG. 1.

As shown in FIG. 4, when the percentage of the tissue region in the tissue image fails to exceed the preset threshold condition, the TGC curve of the tissue image can be calculated in step S205 as follows (steps S501 to S503).

In step S501, an attenuation value of the tissue image can be calculated as follows: attenuation value of tissue image=tissue attenuation coefficient*transmission frequency*image depth.

In step S502, a tissue noise target brightness curve can be calculated, where the tissue noise target brightness curve can be an equal interpolation oblique line between zero and the attenuation value of the tissue image.

In step S503, the TGC curve of the tissue image can be calculated as follows: TGC curve of tissue image=tissue noise target brightness curve−first noise average value curve. A normalized TGC curve can then be obtained by subtracting a curve average value from the calculated TGC curve and performing smoothing filtering.

After obtaining the master gain and the TGC curve through the calculation described above, those calculation results can be applied to the tissue image without the de-noising processing acquired in step 201. At this point, the whole gain optimization has been completed.

In embodiments of this disclosure, the method for optimizing the gain of the ultrasound image can adaptively determine the thresholds for different regions according to the image information, and automatically divide the image into four regions (the boundary one, the tissue one, the low-echo one and the noise one) based on the adaptive thresholds. In this way, the region identification can be more accurate since the differences between the thresholds of different images have been taken into consideration. Also, the method for optimizing the gain can be suitable for various ultrasound images obtained during both the B-mode imaging and the contrast imaging. Moreover, the method for optimizing the gain can be adjusted according to the percentage of the tissue region in the tissue image, which cannot only display the image without information loss but also meet the equalization demand on the brightness of the optimized image.

The gain optimization method as described in the first embodiment can adapt for both the tissue image representing the tissue image during the ultrasound contrast imaging and the fundamental image or the harmonic image during the B-mode imaging. However, during the ultrasound contrast imaging, a contrast image representing contrast agent information can also be generated in addition to the tissue image representing the tissue information. The contrast image may be significantly characterized in that its image brightness can change with the injection and the decreasing of the micro-bubbles. For instance, before the contrast agent is injected, most of the contrast image may be an echoless region, and the whole image except a few strong boundaries may be black. When beginning to inject the contrast agent, only large vessels can be bright enough to be displayed in the image. After entering into an enhancement stage of the contrast agent, all the vessels can be displayed and the whole image may become bright. When the contrast agent decreases gradually, the image brightness may also decrease and may finally return to the condition before the contrast agent was injected. These changes can indicate that the brightness of the contrast image may not be as stable as that of the tissue image, and thus the gain optimization method for the tissue image may not be suitable for the contrast image. Here, a TGC curve of the contrast image can be calculated, however, based on the noise equalization method of the tissue image. This is because no matter how the brightness of the contrast image can change, background noise of the contrast image can be fixed, and thus brightness equalization can be achieved for the contrast image by adjusting a background noise curve. In addition, since the contrast image may mainly reflect micro-bubble information within the tissue vessel and the micro-bubble may have less attenuation when compared with the tissue, the brightness equalization of the contrast image may not be affected by different attenuation of different subjects as the tissue image. For this reason, it can be more suitable to optimize the contrast image according to the noise equalization method.

Figure 5:
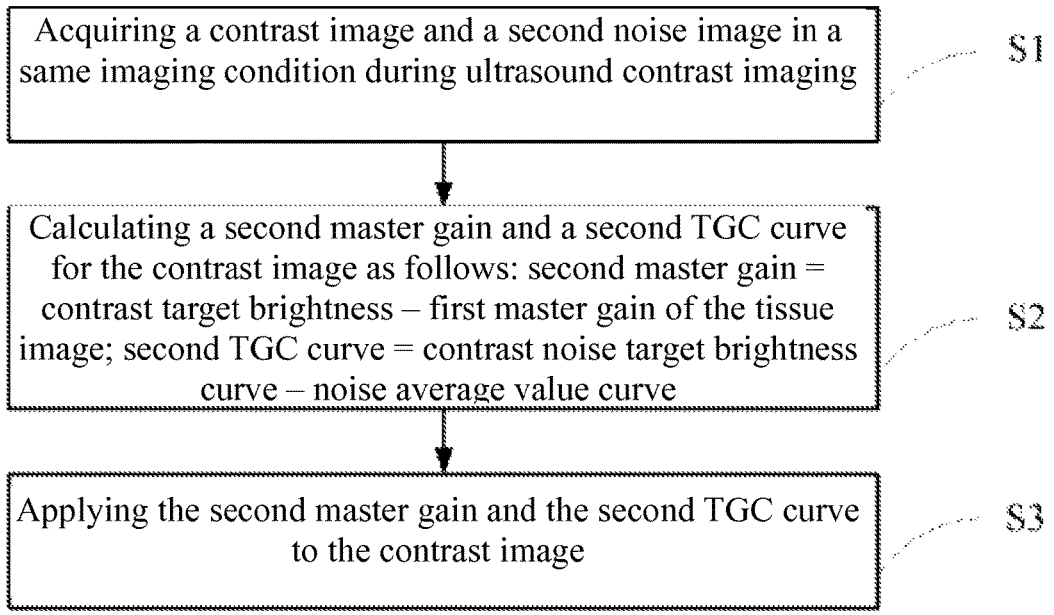
FIG. 5 is a flow chart illustrating a method for optimizing gain of a contrast image in a method for optimizing gain during ultrasound contrast imaging according to a second embodiment of this disclosure.

A method for optimizing gain during ultrasound contrast imaging can be correspondingly provided in a second embodiment of this disclosure. The gain optimization during the ultrasound contrast imaging can include tissue image gain optimization and contrast image gain optimization. In this embodiment, the gain of the tissue image can be optimized according to the method described in the first embodiment, which may not be repeated here. The method for optimizing the gain of the contrast image can include steps S1 to S3 as shown in FIG. 5.

In step S1, the contrast image and a second noise image can be acquired under a same imaging condition during the ultrasound contrast imaging.

In step S2, a master gain and a TGC curve can be calculated for the contrast image.

In step S3, the TGC curve and the master gain of the contrast image obtained through calculation can be applied to the contrast image acquired in step S1.

The master gain of the contrast image can be calculated as follows: providing the contrast image with predetermined gain and correcting the master gain of the contrast image according to the master gain of the tissue image in the contrast imaging mode. That is, the master gain of the contrast image may be substantially equal to a difference value between a contrast target brightness and the master gain of the tissue image, where the master gain of the tissue image may be obtained during the tissue image gain optimization (i.e., master gain of contrast image=target contrast brightness−master gain of tissue image).

In order to display all the contrast images with the same gain, the contrast target brightness of the contrast image can be the predetermined gain. When all the contrast images are displayed using the same gain, those contrast images of some subjects may be too bright while some others may be too dark. The tissue images of different people may be different in the same condition, and so does the contrast image. It can be found that the brightness difference between the tissue images of different subjects may be related to that between the contrast images. Therefore, the master gain of the contrast image can be corrected by the master gain of the tissue image, so that the contrast images of different subjects can have the same brightness after the gain optimization.

Figure 6:
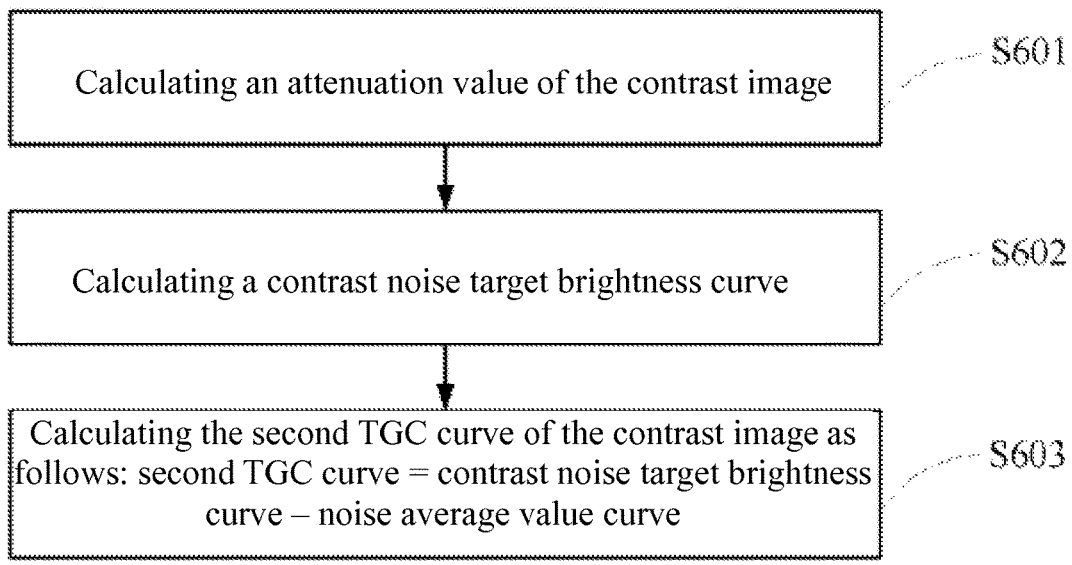
FIG. 6 is a flow chart illustrating the step S2 in FIG. 5.

As shown in FIG. 6, the calculation of the TGC curve of the contrast image may include following steps S601 to S603.

In step S601, an attenuation value of the contrast image can be calculated as follows: attenuation value of contrast image=contrast attenuation coefficient*transmission frequency*image depth.

In step S602, a contrast noise target brightness curve can be calculated, where the contrast noise target brightness curve can be an equal interpolation oblique line between zero and the attenuation value of the contrast image.

In step S603, the TGC curve of the contrast image can be calculated as follows: TGC curve of contrast image=contrast noise target brightness curve−second noise average value curve. A normalized TGC curve can then be obtained by performing smoothing filtering and then subtracting a curve average value from the calculated TGC curve.

After obtaining the master gain and the TGC curve of the contrast image through the calculation described above, those calculation results can be applied to the contrast image acquired in step S1. At this point, the whole contrast image gain optimization has been completed.

Figure 7:
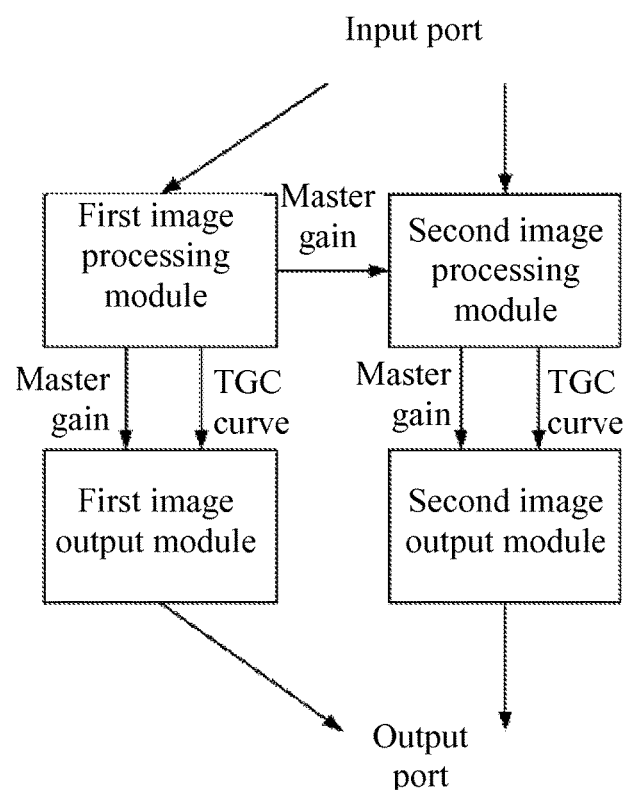
FIG. 7 is a schematic diagram illustrating functional modules for an automatic gain optimization apparatus for ultrasound imaging according to a third embodiment of this disclosure.

As shown in FIG. 7, an automatic gain optimization apparatus for ultrasound imaging can be provided according to a third embodiment of this disclosure. The apparatus can include a first image processing module, a second image processing module, a first image output module and a second image output module. The first image processing module and the second image processing module can connect with an input port, the first image output module and the second image output module can connect with an output port, the first image processing module can connect with the first image output module, the second image processing module can connect with the second image output module, and the first image processing module can also connect with the second image processing module.

The first image processing module can receive image information, calculate a first master gain and a first TGC curve for the tissue image according to the above-described method in the first embodiment of this disclosure, transmit the first TGC curve and the first master gain obtained through calculation to the first image output module, and transmit the first master gain of the tissue image to the second image processing module.

The first image output module can apply the first master gain and the first TGC curve of the tissue image to the acquired tissue image, and output the tissue image with optimized gain through the output port.

The second image processing module can receive the image information, calculate a second master gain and a second TGC curve of the contrast image according to the above-described method in the second embodiment of this disclosure, and transmit the second TGC curve and the second master gain of the contrast image obtained through calculation to the second image output module.

The second image output module can apply the second master gain and the second TGC curve of the contrast image to the acquired contrast image, and output the contrast image with optimized gain through the output port.

The image information can be the fundamental image or the harmonic image and the corresponding noise image obtained during the B-mode imaging. The image information can also be the tissue image and the corresponding noise image obtained during the ultrasound contrast imaging.

In embodiments of this disclosure, when the automatic gain optimization apparatus receives the fundamental image or the harmonic image and the corresponding noise image obtained during the B-mode imaging, the first image processing module and the first image output module may be in operation, while the second image processing module and the second image output module may be in a standby mode. In another situation, when the automatic gain optimization apparatus receives the tissue image, the contrast image and the noise images (which respectively correspond to the tissue image and the contrast image) obtained during the ultrasound contrast imaging, the first image processing module and the first image output module may perform calculation processing according to the tissue image and its corresponding noise image in the contrast mode, and the second image processing module and the second image output module may perform calculation processing according to the contrast image and its corresponding noise image.

The methods and apparatuses for optimizing the gain in this disclosure can further correct the gain adjustment parameter(s) of the contrast image using the gain adjustment parameter(s) of the tissue image obtained in the contrast mode. Compared with the prior art, the contrast images of different subjects can have substantially the same brightness after the gain optimization, thereby improving scan efficiency greatly.

Figure 8:
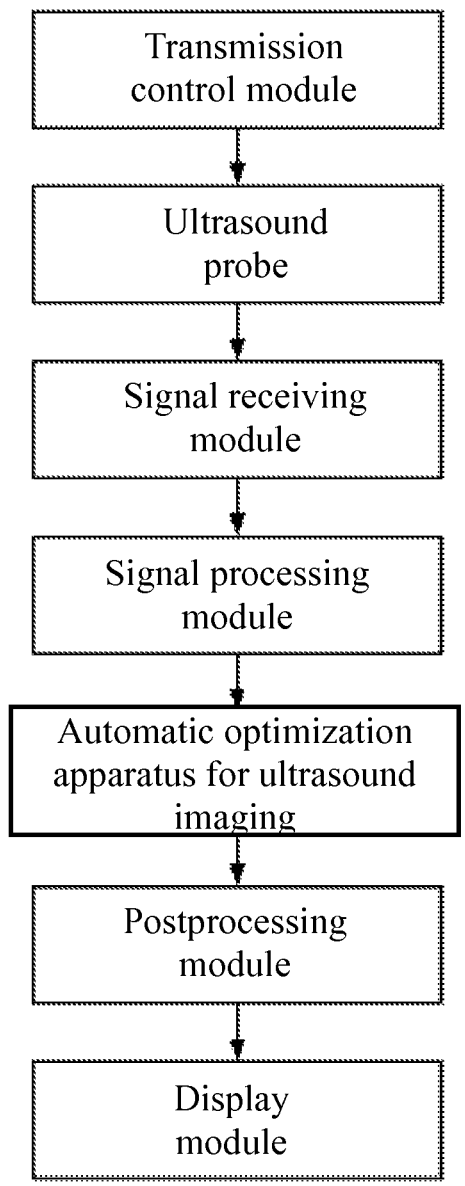
FIG. 8 is a structure diagram for an ultrasound imaging system according to a fourth embodiment of this disclosure.

As shown in FIG. 8, an ultrasound imaging system can further be provided according to a fourth embodiment of this disclosure. The ultrasound imaging system can include a transmission control module, an ultrasound probe, a signal receiving module, a signal processing module, an automatic gain optimization apparatus for ultrasound imaging, a post-processing module and a display module, where those components may connect successively. The ultrasound imaging system may output and display various ultrasound images after different gain optimization.

The ultrasound probe may receive electrical signals transmitted from the transmission control module and convert the electrical signals into voltage signals for generating ultrasound waves to be emitted to a human body. The ultrasound waves can be reflected, refracted and scattered when propagating within the human body, and then ultrasound echoes carrying human tissue characteristics can be returned to the ultrasound probe. After receiving the ultrasound echoes, the ultrasound probe may convert the voltage signals into the electrical signals for transmitting to the signal receiving module. The signal processing module may process the electrical signals received by the signal receiving module to obtain various ultrasound images, where beamforming, filtering, demodulation and envelop solution may be performed for those electrical signals. The signal processing module can then output the fundamental image or the harmonic image and the corresponding noise image during the B-mode imaging. The signal processing module can also output the tissue image, the contrast image and the corresponding noise images during the ultrasound contrast imaging, where the noise images respectively correspond to the contrast image and the tissue image. The ultrasound images can be outputted to the automatic gain optimization apparatus described in the third embodiment of this disclosure for automatic gain optimization processing. In this way, information loss can be avoided and the images can have equalized brightness.

In conventional ultrasound systems, logarithm operation and dynamic range transformation may further be performed on the ultrasound images so that the images may closely fit for human visual observation. Those processing may be completed by the postprocessing module. The processed image may then be displayed through the display module after further scan conversion.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A method for optimizing gain of an ultrasound image within an ultrasound imaging system, the method comprising:

acquiring a tissue image and a first noise image in a same imaging condition using an ultrasound probe;

de-noising the tissue image using a processor based on the first noise image to obtain a de-noised tissue image;
identifying, using the processor, a tissue region in the de-noised tissue image by:
  partitioning the de-noised tissue image into multiple image sub-blocks along a horizontal direction and a longitudinal direction;
  calculating statistical parameters for each image sub-block;
  determining, according to the statistical parameters of each image sub-block, adaptive thresholds to be used for region identification; and
  comparing the statistical parameters of each image sub-block with the adaptive thresholds to determine one of four regions to which each image sub-block belongs, the regions comprising a noise region, a boundary region, a low-echo region or the tissue region;
calculating, using the processor, a first master gain and a first time gain compensation (TGC) curve for the tissue image; wherein, when a percentage of the tissue region in the de-noised tissue image exceeds a preset threshold condition, the first master gain is a difference value between tissue target brightness and an average value of all the tissue regions and the first TGC curve is calculated according to distributions of the tissue region and the noise region;
optimizing, using the processor, the gain of the tissue image by applying the first TGC curve and the first master gain to the tissue image; and
displaying the tissue image with the optimized gain on a display device;
wherein the statistical parameters comprise an average value, a standard deviation and a signal to noise ratio of each image sub-block and the adaptive thresholds comprise a noise threshold, a high threshold for standard deviation, a high threshold for average value and a low threshold for average value;
wherein determining the one of four regions to which each image sub-block belongs comprises:
determining one of the multiple image sub-blocks where the signal to noise ratio is smaller than the noise threshold to be a noise block and thus to belong to the noise region;
determining one of the multiple image sub-blocks where the standard deviation is larger than the high threshold for standard deviation or the average value is larger than the high threshold for average value to be a boundary block and thus to belong to the boundary region;
determining one of the multiple image sub-blocks where the average value is smaller than the low threshold for average value to be a low-echo block and thus to belong to the low-echo region; and
determining one of the multiple image sub-blocks that fails to meet said three determination conditions to be a tissue block and thus to belong to the tissue region.

2. The method of claim 1, wherein:
the noise threshold is manually set according to a signal to noise ratio of the noise region;
the high threshold for standard deviation is calculated as follows:

$TH\mathrm{std}H=\mathrm{mean}(\mathrm{Std}\_Xm)+P*\mathrm{std}(\mathrm{Std}\_Xm);$ the high threshold for average value is calculated as follows:

$TH\mathrm{mean}H=\mathrm{mean}(\mathrm{Mean}\_Xm)+P*\mathrm{std}(\mathrm{Mean}\_Xm);$ the low threshold for average value is calculated as follows:

$TH\mathrm{mean}L=\mathrm{mean}(\mathrm{Mean}\_Xm)-P*\mathrm{std}(\mathrm{Mean}\_Xm);$ wherein Std_Xm represents a standard deviation of an $m^{th}$ image sub-block, mean(Std_Xm) represents an average value of the standard deviations of all the image sub-blocks, std(Std_Xm) represents a total standard deviation of the standard deviations of all the image sub-blocks, Mean_Xm represents an average value of the $m^{th}$ image sub-block, mean(Mean_Xm) represents an average value of the average values of all the image sub-blocks, std(Mean_Xm) represents a standard deviation of the average values of all the image sub-blocks, m is in a range of 1 to M, M represents a total block quantity of the image sub-blocks partitioned from the de-noised tissue image, and P represents an adjustable parameter that is set according to a signal distribution range within the tissue image.

3. The method of claim 2, further comprising removing data of the noise block when calculating the high threshold for standard deviation, the high threshold for average value and the low threshold for average value.

4. The method of claim 2, wherein the adjustable parameter P is inversely proportional to the signal distribution range within the tissue image.

5. The method of claim 1, wherein the percentage of the tissue region in the de-noised tissue image is determined by:
counting a block quantity of the tissue block(s) in each line of the image sub-blocks;
determining a line to be a tissue valid line when a ratio between the block quantity of the tissue block(s) and a block quantity of the image sub-blocks along said line is larger than a first threshold; and
determining the percentage of the tissue region in the de-noised tissue image to exceed the preset threshold condition when a ratio between a line number of all the tissue valid line(s) and a line number of all the image sub-blocks is larger than a second threshold.

6. A method for optimizing gain during ultrasound contrast imaging, comprising performing gain optimization for a tissue image using the method of claim 1, wherein said method further comprises performing gain optimization for a contrast image; the gain optimization for the contrast image comprises:
acquiring the contrast image and a second noise image in a same imaging condition during the ultrasound contrast imaging;
calculating a second master gain and a second TGC curve for the contrast image, wherein the second master gain is substantially equal to a difference value between contrast target brightness and the first master gain of the tissue image; and
applying the second TGC curve and the second master gain obtained through calculation to the contrast image.

7. The method of claim 6, wherein calculating the second TGC curve comprises:
calculating an attenuation value of the contrast image through multiplying a contrast attenuation coefficient by a transmission frequency and image depth;
calculating a contrast noise target brightness curve, wherein the contrast noise target brightness curve is an equal interpolation oblique line between zero and the attenuation value of the contrast image; and
calculating the second TGC curve by subtracting a second noise average value curve from the contrast noise target brightness curve, wherein the second noise average value curve represents average values of each line of the second noise image.

8. The method of claim 1, wherein said tissue image is a tissue image representing tissue information obtained during ultrasound contrast imaging, or said tissue image is a fundamental image or a harmonic image obtained during B-mode imaging.

9. The method of claim 1, wherein de-noising the tissue image based on the first noise image comprises:
calculating an average value of each line of the first noise image to obtain a first noise average value curve; and
subtracting the first noise average value curve from the tissue image to obtain the de-noised tissue image.

10. The method of claim 1, wherein when the percentage of the tissue region in the de-noised tissue image fails to exceed the preset threshold condition, the first master gain is a difference value between a noise target brightness and a minimum value of a longitudinal tissue average value curve; wherein the longitudinal tissue average value curve represents average values of each line of the tissue image.

11. The method of claim 1, wherein when the percentage of the tissue region in the de-noised tissue image fails to exceed the preset threshold condition, the first TGC curve is calculated using a noise equalization method.

12. A method for optimizing gain of an ultrasound image within an ultrasound imaging system, the method comprising:
acquiring a tissue image and a first noise image in a same imaging condition using an ultrasound probe;
de-noising the tissue image using a processor based on the first noise image to obtain a de-noised tissue image;
identifying, using the processor, a tissue region in the de-noised tissue image by:
partitioning the de-noised tissue image into multiple image sub-blocks along a horizontal direction and a longitudinal direction;
calculating statistical parameters for each image sub-block, wherein the statistical parameters comprise an average value, a standard deviation and a signal to noise ratio of each image sub-block;
determining, according to the statistical parameters of each image sub-block, adaptive thresholds to be used for region identification, wherein the adaptive thresholds comprise a noise threshold, a high threshold for standard deviation, a high threshold for average value and a low threshold for average value; and
comparing the statistical parameters of each image sub-block with the adaptive thresholds to determine one of four regions to which each image sub-block belongs, the regions comprising a noise region, a boundary region, a low-echo region or the tissue region;
calculating, using the processor, a first master gain and a first time gain compensation (TGC) curve for the tissue image; wherein, when a percentage of the tissue region in the de-noised tissue image exceeds a preset threshold condition, the first master gain is a difference value between tissue target brightness and an average value of all the tissue regions and the first TGC curve is calculated according to distributions of the tissue region and the noise region; wherein, when the percentage of the tissue region in the de-noised tissue image fails to exceed the preset threshold condition, the first master gain is a difference value between a noise target brightness and a minimum value of a longitudinal tissue average value curve; wherein the longitudinal tissue average value curve represents average values of each line of the tissue image;
optimizing, using the processor, the gain of the tissue image by applying the first TGC curve and the first master gain to the tissue image; and displaying the tissue image with the optimized gain on a display device.

13. A method for optimizing gain during ultrasound contrast imaging, comprising performing gain optimization for a tissue image using the method of claim 12, wherein said method further comprises performing gain optimization for a contrast image; the gain optimization for the contrast image comprises:
acquiring the contrast image and a second noise image in a same imaging condition during the ultrasound contrast imaging;
calculating a second master gain and a second TGC curve for the contrast image, wherein the second master gain is substantially equal to a difference value between contrast target brightness and the first master gain of the tissue image; and
applying the second TGC curve and the second master gain obtained through calculation to the contrast image.

14. A method for optimizing gain of an ultrasound image within an ultrasound imaging system, the method comprising:
acquiring a tissue image and a first noise image in a same imaging condition using an ultrasound probe;
de-noising the tissue image using a processor based on the first noise image to obtain a de-noised tissue image;
identifying, using the processor, a tissue region in the de-noised tissue image by:
partitioning the de-noised tissue image into multiple image sub-blocks along a horizontal direction and a longitudinal direction;
calculating statistical parameters for each image sub-block, wherein the statistical parameters comprise an average value, a standard deviation and a signal to noise ratio of each image sub-block;
determining, according to the statistical parameters of each image sub-block, adaptive thresholds to be used for region identification, wherein the adaptive thresholds comprise a noise threshold, a high threshold for standard deviation, a high threshold for average value and a low threshold for average value; and
comparing the statistical parameters of each image sub-block with the adaptive thresholds to determine one of four regions to which each image sub-block belongs, the regions comprising a noise region, a boundary region, a low-echo region or the tissue region;
calculating, using the processor, a first master gain and a first time gain compensation (TGC) curve for the tissue image; wherein, when a percentage of the tissue region in the de-noised tissue image exceeds a preset threshold condition, the first master gain is a difference value between tissue target brightness and an average value of all the tissue regions and the first TGC curve is calculated according to distributions of the tissue region and the noise region; wherein when the percentage of the tissue region in the de-noised tissue image fails to exceed the preset threshold condition, the first TGC curve is calculated using a noise equalization method;

optimizing, using the processor, the gain of the tissue image by applying the first TGC curve and the first master gain to the tissue image; and displaying the tissue image with the optimized gain on a display device.

15. The method of claim 14, wherein when the percentage of the tissue region in the de-noised tissue image exceeds the preset threshold condition, calculating the first TGC curve comprises:

calculating a longitudinal average value curve, said calculating comprises taking an average value of the tissue blocks in a tissue valid line as a value of the longitudinal average value curve corresponding to said tissue valid line; taking an average value of the noise blocks in a noise valid line as a value of the longitudinal average value curve corresponding to said noise valid line; taking an average value of the tissue blocks in a line as a value of the longitudinal average value curve corresponding to said line when said line is both a tissue valid line and a noise valid line; and taking a linear interpolation of other line(s) as a value of the longitudinal average value curve corresponding to said other line(s) when said other line(s) is(are) neither a tissue valid line nor a noise valid line; wherein the linear interpolation of said other line(s) is(are) obtained using an average value of the tissue valid line(s) and/or the noise valid line(s) that is(are) adjacent to said other line(s); wherein the noise valid line is defined as a ratio between a block quantity of the noise block(s) and the block quantity of the image sub-blocks in the noise valid line is larger than the first threshold;

calculating a target brightness curve, said calculating comprises determining target brightness of each line according to image property of said each line; wherein target brightness of the tissue valid line is substantially equal to tissue target brightness, target brightness of the noise valid line is substantially equal to noise target brightness, and target brightness of other line(s) is obtained through interpolation using the target brightness of the tissue valid line(s) and/or noise valid line(s); and calculating the first TGC curve by subtracting a first noise average value curve and the longitudinal average value curve from the target brightness curve, wherein the first noise average value curve represents average values of each line of the first noise image.

16. The method of claim 14, wherein when the percentage of the tissue region in the de-noised tissue image fails to exceed the preset threshold condition, calculating the first TGC curve comprises:

calculating an attenuation value of the tissue image through multiplying a tissue attenuation coefficient by a transmission frequency and image depth;

calculating a tissue noise target brightness curve, wherein the tissue noise target brightness curve is an equal interpolation oblique line between zero and the attenuation value of the tissue image; and calculating the first TGC curve by subtracting a first noise average value curve from the tissue noise target brightness curve, wherein the first noise average value curve represents average values of each line of the first noise image.

17. A method for optimizing gain during ultrasound contrast imaging, comprising performing gain optimization for a tissue image using the method of claim 14, wherein said method further comprises performing gain optimization for a contrast image; the gain optimization for the contrast image comprises:

acquiring the contrast image and a second noise image in a same imaging condition during the ultrasound contrast imaging;

calculating a second master gain and a second TGC curve for the contrast image, wherein the second master gain is substantially equal to a difference value between contrast target brightness and the first master gain of the tissue image; and applying the second TGC curve and the second master gain obtained through calculation to the contrast image.

18. An ultrasound imaging system comprising:

an ultrasound probe that acquires a tissue image and a first noise image in a same imaging condition;

a processor configured to:
  denoise the tissue image based on the first noise image to obtain a de-noised tissue image;
  identify a tissue region in the de-noised tissue image by:
    partitioning the de-noised tissue image into multiple image sub-blocks along a horizontal direction and a longitudinal direction;
    calculating statistical parameters for each image sub-block;
    determining, according to the statistical parameters of each image sub-block, adaptive thresholds to be used for region identification; and
    comparing the statistical parameters of each image sub-block with the adaptive thresholds to determine one of four regions to which each image sub-block belongs, the regions comprising a noise region, a boundary region, a low-echo region or the tissue region;
  calculate a first master gain and a first time gain compensation (TGC) curve for the tissue image; wherein, when a percentage of the tissue region in the de-noised tissue image exceeds a preset threshold condition, the first master gain is a difference value between tissue target brightness and an average value of all the tissue regions and the first TGC curve is calculated according to distributions of the tissue region and the noise region;
  optimize the gain of the tissue image by applying the first TGC curve and the first master gain to the tissue image; and a display that outputs the tissue image with the optimized gain;

wherein the statistical parameters comprise an average value, a standard deviation and a signal to noise ratio of each image sub-block and the adaptive thresholds comprise a noise threshold, a high threshold for standard deviation, a high threshold for average value and a low threshold for average value;

wherein the processor determines the one of four regions to which each image sub-block belongs by:
  determining one of the multiple image sub-blocks where the signal to noise ratio is smaller than the noise threshold to be a noise block and thus to belong to the noise region;
  determining one of the multiple image sub-blocks where the standard deviation is larger than the high threshold for standard deviation or the average value is larger than the high threshold for average value to be a boundary block and thus to belong to the boundary region;

determining one of the multiple image sub-blocks where the average value is smaller than the low threshold for average value to be a low-echo block and thus to belong to the low-echo region; and determining one of the multiple image sub-blocks that fails to meet said three determination conditions to be a tissue block and thus to belong to the tissue region.

19. The system of claim 18, wherein the image processor determines whether the percentage of the tissue region in the de-noised tissue image exceeds the preset threshold condition by:

counting a block quantity of the tissue block(s) in each line of the image sub-blocks;

determining a line to be a tissue valid line when a ratio between the block quantity of the tissue block(s) and a block quantity of the image sub-blocks along said line is larger than a first threshold; and determining the percentage of the tissue region in the de-noised tissue image to exceed the preset threshold condition when a ratio between a line number of all the tissue valid line(s) and a line number of all the image sub-blocks is larger than a second threshold.

20. An ultrasound imaging system comprising:

an ultrasound probe that acquires a tissue image and a first noise image in a same imaging condition;

a processor configured to:
  denoise the tissue image based on the first noise image to obtain a de-noised tissue image;
  identify a tissue region in the de-noised tissue image by:
    partitioning the de-noised tissue image into multiple image sub-blocks along a horizontal direction and a longitudinal direction;
    calculating statistical parameters for each image sub-block, wherein the statistical parameters comprise an average value, a standard deviation and a signal to noise ratio of each image sub-block;
    determining, according to the statistical parameters of each image sub-block, adaptive thresholds to be used for region identification, wherein the adaptive thresholds comprise a noise threshold, a high threshold for standard deviation, a high threshold for average value and a low threshold for average value; and
    comparing the statistical parameters of each image sub-block with the adaptive thresholds to determine one of four regions to which each image sub-block belongs, the regions comprising a noise region, a boundary region, a low-echo region or the tissue region;
  calculate a first master gain and a first time gain compensation (TGC) curve for the tissue image; wherein, when a percentage of the tissue region in the de-noised tissue image exceeds a preset threshold condition, the first master gain is a difference value between tissue target brightness and an average value of all the tissue regions and the first TGC curve is calculated according to distributions of the tissue region and the noise region; wherein, when the percentage of the tissue region in the de-noised tissue image fails to exceed the preset threshold condition, the first master gain is a difference value between a noise target brightness and a minimum value of a longitudinal tissue average value curve; wherein the longitudinal tissue average value curve represents average values of each line of the tissue image;
  optimize the gain of the tissue image by applying the first TGC curve and the first master gain to the tissue image; and
a display that outputs the tissue image with the optimized gain.

21. An ultrasound imaging system comprising:

an ultrasound probe that acquires a tissue image and a first noise image in a same imaging condition;

a processor configured to:
  denoise the tissue image based on the first noise image to obtain a de-noised tissue image;
  identify a tissue region in the de-noised tissue image by:
    partitioning the de-noised tissue image into multiple image sub-blocks along a horizontal direction and a longitudinal direction;
    calculating statistical parameters for each image sub-block, wherein the statistical parameters comprise an average value, a standard deviation and a signal to noise ratio of each image sub-block;
    determining, according to the statistical parameters of each image sub-block, adaptive thresholds to be used for region identification, wherein the adaptive thresholds comprise a noise threshold, a high threshold for standard deviation, a high threshold for average value and a low threshold for average value; and
    comparing the statistical parameters of each image sub-block with the adaptive thresholds to determine one of four regions to which each image sub-block belongs, the regions comprising a noise region, a boundary region, a low-echo region or the tissue region;
  calculate a first master gain and a first time gain compensation (TGC) curve for the tissue image; wherein, when a percentage of the tissue region in the de-noised tissue image exceeds a preset threshold condition, the first master gain is a difference value between tissue target brightness and an average value of all the tissue regions and the first TGC curve is calculated according to distributions of the tissue region and the noise region; wherein when the percentage of the tissue region in the de-noised tissue image fails to exceed the preset threshold condition, the first TGC curve is calculated using a noise equalization method;
  optimize the gain of the tissue image by applying the first TGC curve and the first master gain to the tissue image; and
a display that outputs the tissue image with the optimized gain.

* * * * *